United States Patent [19]

Peck et al.

[11] Patent Number: 4,576,702
[45] Date of Patent: Mar. 18, 1986

[54] ANALYTICAL ELECTROELUTION DEVICE

[75] Inventors: Lawrence J. Peck, Cambridge, Mass.; John H. Kreisher, Ridgefield, Conn.

[73] Assignee: International Biotechnologies, Inc., New Haven, Conn.

[21] Appl. No.: 668,562

[22] Filed: Nov. 5, 1984

[51] Int. Cl.⁴ .......................................... G01N 27/28
[52] U.S. Cl. .............................. 204/299 R; 204/182.8
[58] Field of Search ............ 204/299 R, 180 G, 182.8

[56] References Cited

U.S. PATENT DOCUMENTS 3,989,612  11/1976  Kragt et al. ...................... 204/299 R
4,049,534  9/1977   Posner ............................. 204/180 G

FOREIGN PATENT DOCUMENTS 552373  4/1977  U.S.S.R. ..

OTHER PUBLICATIONS

Diekmann, S., "A Device to Flute Biomolecules Out of Gels", *Electrophoresis '84*, Editor: Volker Neuhoff, pp. 154–155, Jul. 1984.

*Primary Examiner*—John F. Niebling
*Assistant Examiner*—B. J. Boggs, Jr.
*Attorney, Agent, or Firm*—Bachman & La Pointe

[57] ABSTRACT

A simplified electroelution receptacle designed to receive and process a plurality of small biological samples simultaneously facilitating efficient recovery of biological particles in a highly concentrated manner with a minimum of undesirable liquid.

12 Claims, 4 Drawing Figures

ANALYTICAL ELECTROELUTION DEVICE

BACKGROUND OF THE INVENTION

The present invention relates to electrophoresis and relates in particular to a novel receptacle or apparatus for removing (eluting) and collecting charged particles of biological substances from gel slices in highly concentrated forms and with a bare minimum of undesirable liquid.

The procedure is referred to hereinafter as electroelution.

The present invention is an improvement over a copending application filed Nov. 5, 1984 by Peck et al. entitled Preparatory Electroelution Device bearing Ser. No. 668,571 both applications having a common Assignee.

The isolation of DNA, RNA, carbohydrates and proteins from electrophoresis gels has been a long standing problem. Several methods are available for recovering nucleic acids from acrylamide and agarose gels. These include (1) elution by diffusion, (2) extrusion by compression, (3) gel dissolution, and (4) electroelution. Most of these systems result in poor yield, degradation, contaminated end products, and are very cumbersome to operate. Electroelution is often the best method, although up to now, made difficult by the necessity for membranes, tube gels and related paraphernalia. In electroelution systems, the biologicals can stick to the membranes when dialysis tubing or membrane systems are used. A reverse current will partially release the material, but the process is not quantitative. Smaller fragments may pass through the membrane. Tube gels and related electrophoresis systems are cumbersome to operate.

The present invention provides an improved apparatus useful to carry out electroelution procedures in a manner which eliminates many of the difficulties encountered in prior art structures.

In the improved device an array of sample supports are provided facilitating the removal and collection of biological particles from a number of samples simultaneously.

Treatment of multiple samples simultaneously saves time of highly trained technical personnel and provides a series of results from a given family of samples in a very convenient fashion facilitating subsequent procedural steps.

Consequently it is a prime object of the present invention to provide an efficient electroelution device.

It is a further object to provide a device which is operative to recover and collect small particles or fragments of particles which would pass through and be lost in membrane arrangements of the prior art.

For example, the present invention is operable to concentrate masses of particles of the order of 10 to 20 micrograms in a liquid volume as small as 200 microliters.

A further feature of the invention is the provision of a novel electroelution receptacle structure which is accessable, convenient to operate, purge and keep clean.

SUMMARY OF THE INVENTION

An electroelution device or receptacle embracing certain principles of the invention may comprise at least two fluid tight compartments separated by a bridge element, said bridge element being formed with a plurality of spaced recesses defining sample supports, said bridge being further formed with a plurality of conduits, one conduit being individual to each sample support and each conduit having a first outlet communicating with a mating sample support and a second outlet communicating with one of said compartments.

BRIEF DESCRIPTION OF THE DRAWINGS

Other features and advantages of the present invention will become more apparent from an examination of the appended drawings, in which.

DETAILED DESCRIPTION

Figure 1:
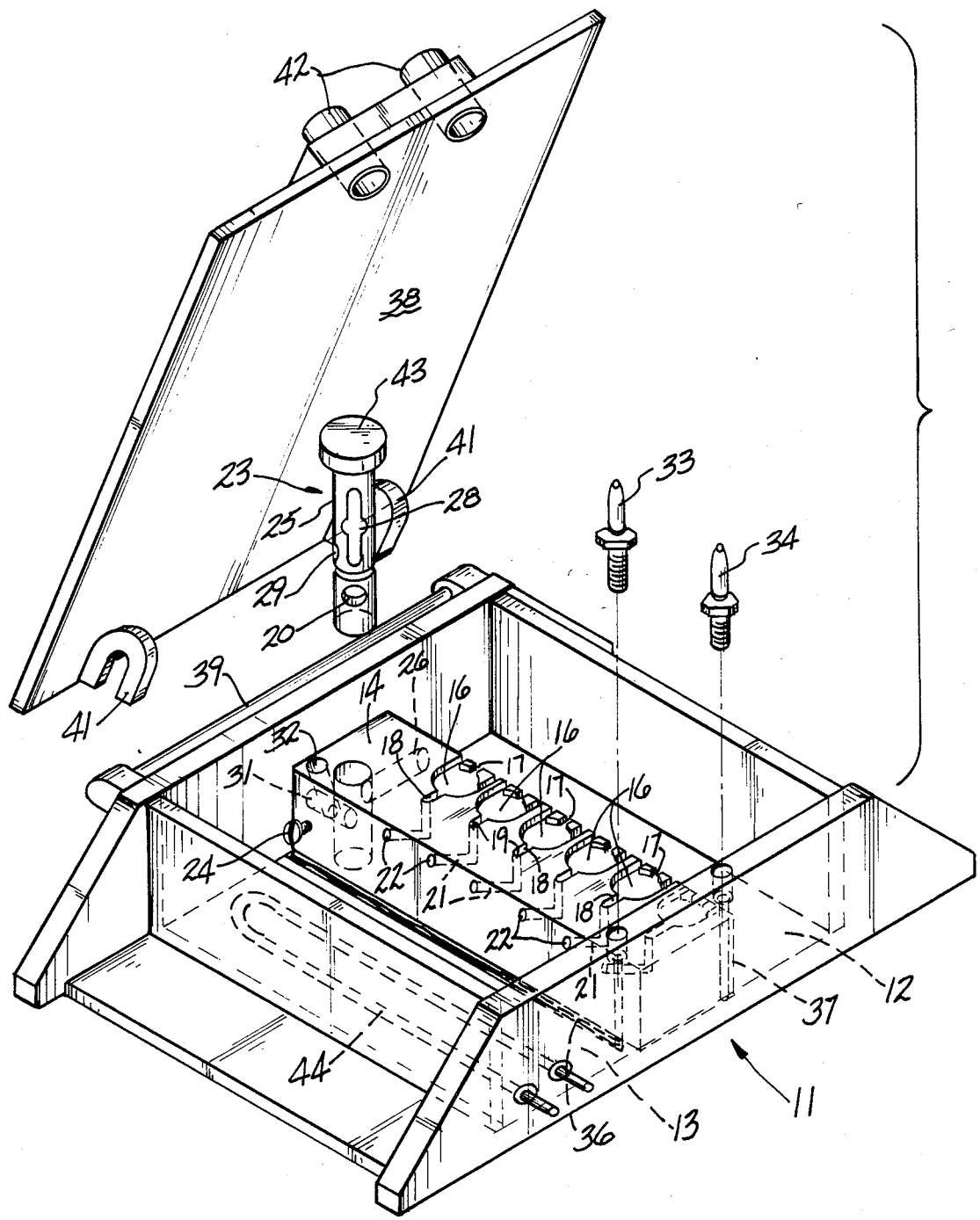
FIG. 1 is an exploded view in perspective of an electroelution device illustrating the principles of this invention.
Figure 2:
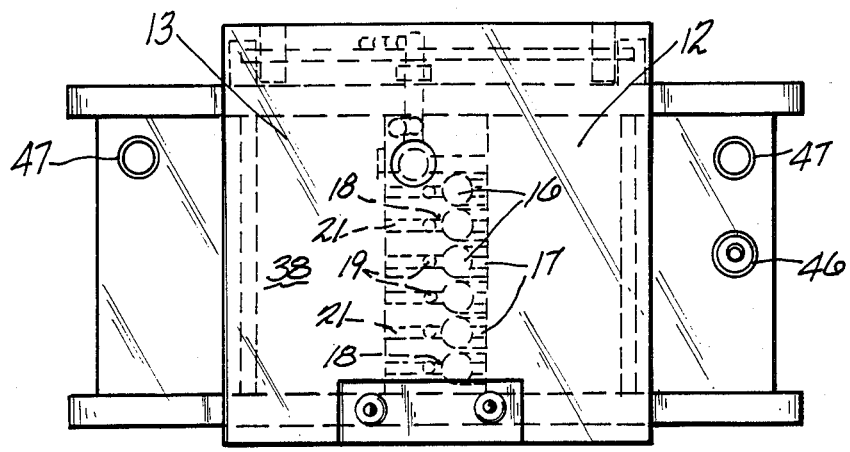
FIG. 2 is a top plan view.
Figure 3:
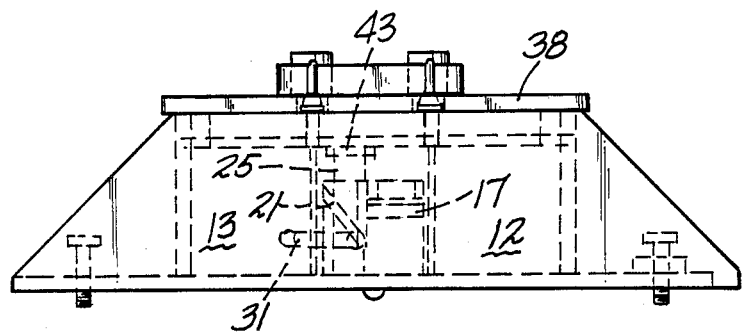
FIG. 3 is a front elevation of FIG. 2.
Figure 4:
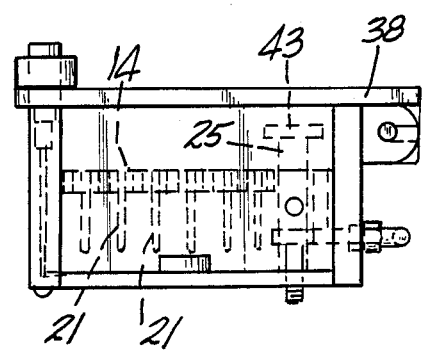
FIG. 4 is an elevational view of the right side of FIG. 2.

Referring now in detail to the drawings the electroelution device, indicated generally by the reference numeral 11, includes a first compartment 12, a second compartment 13 separated by a bridge element 14.

The bridge element 14 is formed with an array of spaced recesses 16—16 defining sample supports or sample receptacles.

Each recess 16 is formed with a first cut-out or sluice way 17 directed to compartment 12 and a second, opposed cut-out 18 directed to an outlet 19 of a conduit 21.

The conduit 21 is generally V-shaped and terminates in an outlet 22 opening into compartment 13.

The outlets 19—19 lie generally in the same plane and are offset vertically above coplanar outlets 22—22.

The tip or low point of the conduit 21 is spaced vertically and below all outlets 19 and 22.

A three position valve, indicated generally at 23, is movable selectively from a first position in which compartments 12 and 13 communicate through the valve stem opening 20 and opposed bridge ports 24 and 26, to a second position in which the valve stem 27 cuts off compartment communication, to a third position in which both compartments 12 and 13 communicate to atmosphere through stem openings 28 and 19 and conduit 31 in the manner described in similar detail in said copending application.

The bridge element 14 also includes an overflow port 32 which by-passes valve 23 and also communicates with atmosphere through conduit 31.

Electrical connectors 33-34 supply current to mating electrodes 36 and 37 disposed in the bottom of each compartment.

A cover 38 hinged to rod 39 by U-shaped clips 41—41 is fitted with ferrules 42—42 providing access for the electrodes 36 and 37.

The cooperation between the cover 38 and head 43 of valve stem 25 and the control of the stroke of the stem 25 are as disclosed and described in said copending application.

In order to control temperature when temperature sensitive materials are involved, one or both of the compartments 12 and 13 are provided with coolant coils 44 indicated in dotted lines in FIG. 1.

A carpenter's level 45 with appropriate levelling screws 47—47 is provided to level the surface of fluid within compartments 12 and 13.

The electroelution device operates in the following fashion:

The valve 23 is elevated to its first position in which there is communication between both compartments 12 and 13, and the unit is levelled. Next, appropriate buffer liquid is introduced into one of the other compartments filling the compartments until overflow occurs to atmosphere at overflow port 32. This overflow occurrence establishes the proper level of buffer liquid.

Thereafter a specific salt of predetermined density (of substantially greater density than the density of the buffer liquid) is pipetted into each V-shaped conduit 21—21. This step displaces the lower gravity buffer liquid from the V-shaped conduits. Next samples are distributed into the array of sample supports 16—16.

The cover 38 is closed causing valve 23 to move to the second position cutting off communication between compartments 12 and 13.

Electrical potential is applied to connectors 33-34 and the electroelution procedures begins and continues for an appropriate interval.

Recovered particles collect upon the surface of the dense salt contained in the V-shaped conduits.

When the collection procedure is completed the power is disconnected and the valve 23 moved to its third position permitting buffer liquid to drain to atmosphere isolating the matter in the V-shaped conduits.

Thereafter the contents of the V-shaped conduits are removed by pipetting for further treatment.

As stated previously if the samples are heat sensitive it is sometimes necessary to run coolant through coolant tubes—to maintain desired temperature gradient.

It is to be understood that the invention is not limited to the illustrations described and shown herein, which are deemed to be merely illustrative of the best modes of carrying out the invention, and which are susceptible of modification of form, size, arrangement of parts and details of operation. The invention rather is intended to encompass all such modifications which are within its spirit and scope as defined by the claims.

We claim:

1. An electroelution device for removing and collecting charged biological particles from a plurality of small gel slices or samples simultaneously comprising at least two fluid tight compartments separated by a bridge element, said bridge element being formed with a plurality of spaced recesses defining sample supports, said bridge being further formed with a plurality of conduits, one conduit being individual to each sample support and each conduit having a first outlet communicating with a mating sample support and a second outlet communicating with one of said compartments.

2. The device of claim 1 in which the first and second outlets are offset from one another.

3. The device of claim 2 in which the first outlets are coplanar and are offset vertically from the second outlets.

4. The device of claim 3 in which the first outlets are elevated relative to the disposition of the second outlets.

5. The device of claim 4 in which the conduits define a generally V-shaped configuration between outlets.

6. The device of claim 5 in which a portion of each conduit is offset vertically relative to the elevation of all outlets.

7. The device of claim 6 in which the conduits are generally V-shaped and the apex of the V is lower in elevation than the elevation of all outlets.

8. The device of claim 7 in which the bridge element is fitted with a valve means which includes ports which communicates selectively with both compartments and with the atmosphere.

9. The device of claim 8 in which the valve means is settable (a) to a first position in which opposed ports provide communication between both compartments, (b) to a second position in which said communication is cut-off, (c) to a third position in which said opposed ports and thus the compartments communicate with the atmosphere.

10. The device of claim 9 in which the bridge element is provided with an overflow port which provides a by-pass to the atmosphere independently of the valve means.

11. The device of claim 10 in which each compartment is fitted with an electrode leading to a fixed electrical connection mounted in the receptacle.

12. The device of claim 11 in which at least one compartment is fitted with cooling tubes for the circulation of coolant for controlling temperature.

* * * * *